(12) United States Patent
Lieberman (10) Patent No.: US 6,197,531 B1
(45) Date of Patent: Mar. 6, 2001

(54) METHOD FOR DETERMINING THE IMMUNOCOMPETENCE OF A MAMMAL AND THERAPIES RELATED THERETO

(75) Inventor: Judy Lieberman, Brookline, MA (US)

(73) Assignee: Center For Blood Research, Inc., Boston, MA (US)

( * ) Notice: Subject to any disclaimer, the term of this patent is extended or adjusted under 35 U.S.C. 154(b) by 0 days.

(21) Appl. No.: 09/009,958

(22) Filed: Jan. 21, 1998

Related U.S. Application Data (60) Provisional application No. 60/036,267, filed on Jan. 22, 1997, now abandoned.

(51) Int. Cl.$^7$ .................................................... G01N 33/53
(52) U.S. Cl. ...................... 435/7.24; 435/7.2; 435/7.21; 435/40.5; 435/40.51; 435/40.52
(58) Field of Search ............................ 435/7.2, 7.21, 435/7.24, 40.5, 40.51, 40.52

(56) References Cited

U.S. PATENT DOCUMENTS 5,296,353   3/1994   Ochoa et al. ..................... 435/7.23

OTHER PUBLICATIONS

Matsuda et al., *Int. J. Cancer* 61:765–772, 1995.*

Gunji et al., High Frequency of Cancer Patients with Abnormal Assembly of the T Cell Receptor–CD3 Complex in Peripheral Blood T Lymphocytes, Jpn. J. Cancer Res 85:1189–1192 (1994).

Finke et al., Loss of T–Cell Receptor ζ Chain and p56$^{lck}$ in T–Cells Infiltrating Human Renal Cell Carcinoma, Cancer Research 53:5613–5616 (1993).

Nakagomi et al., Decreased Expression of the Signal–transducing ζ Chains in Tumor–infiltrating T–Cells and NK Cells of Patients with Colorectal Carcinoma, Cancer Research 53:5610–5612 (1993).

Stefanova et al., HIV Infection–induced Posttranslational Modification of T Cell Signaling Molecules Associated with Disease Progression, J. Chin. Invest. 98:1290–1297 (1996).

Lieberman et al., Ex Vivo Expansion of HIV Type 1–Specific Cytolytic T Cells from HIV Type 1–Seropositive Subjects, Aids Research and Human Retroviruses 11:257–271 (1995).

Renner et al., T Cells From Patients With Hodgkin's Disease Have A Defective T–Cell Receptor ζ Chain Expression That Is Reversible By T–Cell Stimulation With CD3 and CD28, Blood 88:236–241 (1996).

Weiss and Littmann, Signal Transduction by Lymphocyte Antigen Receptors, Cell 76–263–274 (1994).

Lieberman et al., Cytotoxic T–Lymphocytes from HIV–1 Seropositive Individuals Recognize Immunodominant Epitopes in Gp160 and Reverse Transcriptase, J. Immunol. 148:2738–2747 (1992).

Anderson et al., Monoclonal Antibodies Reactive with the T Cell Receptor ζ Chain:Production and Characterization using a New Method, J. Immunol. 143:1899–1904 (1989).

* cited by examiner

*Primary Examiner*—Robert D. Budens
(74) *Attorney, Agent, or Firm*—Fish & Richardson P.C.

(57) ABSTRACT

A method for determining the immunocompetence of a mammal is described. Bodily fluid having T cell receptor complexes from a mammal is provided. Expression of a first component and a second component of the T cell receptor complexes is evaluated. An abnormal ratio of the number of cells expressing the first component as compared to the number of cells expressing the second component indicates altered immunocompetence in the mammal. Also described are methods for monitoring a therapeutic treatment of a disease in a mammal associated with an abnormal level of a T cell receptor complex component, methods for assessing the progression of a disease in a mammal associated with an abnormal level of a T cell receptor complex component, methods for predicting the prognosis of a mammal having a disease associated with an abnormal level of a T cell receptor complex component, methods for determining if a mammal is at risk for AIDS, methods for evaluating an agent for use in treating HIV infection, and methods for treating HIV infection in a mammal. Pharmaceutical compositions and kits are also provided.

19 Claims, 6 Drawing Sheets

METHOD FOR DETERMINING THE IMMUNOCOMPETENCE OF A MAMMAL AND THERAPIES RELATED THERETO

This application claims the benefit of U.S. Provisional Application No. 60/036,267 filed Jan. 22, 1997, now abandoned.

The U.S. Government has a paid-up license in this invention and the right in limited circumstances to require the patent owner to license others on reasonable terms as provided for by the terms of Grant No. AI36611 awarded by National Institutes of Health, National Institutes of Allergy and Infectious Diseases.

FIELD OF THE INVENTION

This invention relates generally to determining the immunocompetence of a mammal and to treatments, prognoses and pharmaceutical compositions for diseases exhibiting deficient immunocompetence, e.g., HIV infection.

BACKGROUND OF THE INVENTION

Cytotoxic T-lymphocyte cells play a central role in the biological defense against what are commonly considered irreversible, pathogenic infections with human immunodeficiency virus (HIV). It is believed that, as a consequence of HIV infection, cytotoxic T-lymphocyte cells are recruited to limit the spread of viral infection by recognizing and lysing viral-infected cells. A central role in the expression of anti-viral activity of cytotoxic T-lymphocyte cells is played by a cell surface molecular receptor signaling process whereby cell surface sensing proteins detect the presence of HIV peptides contained in the viral envelope or viral-specific enzymes.

In HIV-infected individuals who have not developed AIDS opportunistic infections, there is a high frequency of circulating T cells bearing T cell receptors that recognize HIV-infected cells. Despite the vigorous expansion of anti-viral T cells which can develop into cytotoxic effector cells capable of lysing HIV-infected targets and which secrete soluble factors capable of suppressing HIV replication, the cellular immune response eventually becomes unable to control viral production, the HIV-infected individual having become deficient in immunocompetence.

SUMMARY OF THE INVENTION

It is an object of the invention to provide a safe, easy and inexpensive method for determining the immunocompetence of a mammal.

It is another object of the invention to provide a method for determining the immunocompetence of a mammal which uses non-viable and non-radioactive specimens and reagents.

It is another object of the invention to provide a safe, easy and inexpensive method for monitoring a therapeutic treatment of a disease such as HIV.

It is another object of the invention to provide a safe, easy and inexpensive method for assessing the progression of a disease such as HIV.

Still another object of the invention is to provide methods for treating HIV infection in a mammal.

In one aspect, the invention features a method for determining the immunocompetence of a mammal. Bodily fluid having cells from a mammal, the cells having T cell receptor complexes, is provided. The expression of a first component, e.g., CD3$\zeta$, and a second component, e.g., CD3$\epsilon$, of the T cell receptor complexes, is evaluated. An abnormal ratio of the number of cells expressing the first component as compared to the number of cells expressing the second component indicates altered immunocompetence in the mammal.

In preferred embodiments, evaluation of expression of the first component and the second component of the T cell receptor complexes comprises contacting a first sample of the bodily fluid from the mammal with a first antibody that binds to the first component, and contacting a second sample of the bodily fluid with a second antibody that binds to the second component, under conditions which allow for formation of a first reaction complex comprising the first component and the first antibody, and a second reaction complex comprising the second component and the second antibody. The number of cells expressing the first and second complexes formed is detected. The number of cells expressing the first reaction complex corresponds to the level of the first component in the bodily fluid sample, and the number of cells expressing the second reaction complex corresponds to the level of the second component in the bodily fluid sample. The ratio of the number of cells expressing the first reaction complexes formed to the number of cells expressing the second reaction complexes formed is determined. An abnormal ratio of the number of cells expressing the first component as compared to the number of cells expressing the second component indicates altered immunocompetence in the mammal. Preferably, the antibodies are labeled with fluorescent reagents, and preferably, detection of the amount of first and second reaction complexes formed is by flow cytometry.

Another aspect of the invention is a method for monitoring a therapeutic treatment of a disease in a mammal associated with an abnormal level of a first T cell receptor complex component, e.g., HIV infection, Hodgkin's disease or a solid tumor. The ratio of cells expressing the first T cell receptor complex component and a second T cell receptor complex component in a plurality of bodily fluid samples having cells obtained at different time points from a mammal undergoing a therapeutic treatment for a disease associated with an abnormal level of the first T cell receptor complex component, is determined. A ratio that has become more normal is indicative of an effective therapeutic treatment. Preferably, the first component is CD3$\zeta$. Preferably, the second component is CD3$\epsilon$.

Another aspect of the invention is a method for assessing the progression of a disease in a mammal associated with an abnormal level of a first T cell receptor complex component. The ratio of cells expressing the first T cell receptor complex component and a second T cell receptor complex component in a plurality of blood samples having cells obtained at different time points from the mammal is determined. A ratio that becomes more abnormal is indicative of progression of the disease, and a ratio that becomes more normal is indicative of regression of the disease.

Another aspect of the invention is a method for predicting the prognosis of a mammal having a disease which is associated with an abnormal level of a first T cell receptor complex component. The ratio of cells expressing the first T cell receptor complex component and a second T cell receptor complex component in a plurality of bodily fluid samples having cells obtained at different time points from the mammal is determined. A ratio that becomes more abnormal is indicative of a negative prognosis for the mammal, and a ratio that becomes more normal is indicative of a positive prognosis for the mammal.

Another aspect of the invention is a method for determining if a mammal is at risk for AIDS. Bodily fluid having cells from a mammal, the cells having T cell receptor complexes, and the mammal being infected with HIV, is provided. The ratio of cells expressing a first T cell receptor complex component and a second T cell receptor complex component is determined. An abnormal ratio is diagnostic of being at risk for AIDS.

Another aspect of the invention is a method for evaluating an agent for use in treating HIV infection. A mammal infected with HIV is provided. The mammal has an abnormal ratio of the number of cells expressing a first T cell receptor complex component as compared to the number of cells expressing a second T cell receptor complex component. An agent is provided. The agent is administered to the mammal in a therapeutically effective amount. The effect of the agent on the ratio of the number of cells expressing the first T cell receptor complex component as compared to the number of cells expressing the second T cell receptor complex component is evaluated. A change in the ratio is indicative of the usefulness of the agent in treating HIV infection.

Another aspect of the invention is a method for treating HIV infection in a mammal. A mammal having T cell receptor complexes and in need of treatment for HIV infection is provided. An agent capable of altering the expression of a signaling component of the T cell receptor complex is provided. The agent is administered to the mammal in a therapeutically effective amount such that treatment of the HIV infection occurs.

Another aspect of the invention is a method for treating HIV infection in a mammal. A mammal having T cell receptor complexes and in need of treatment for HIV infection is provided. T cells which have been cultured under conditions so as to increase the expression of a signaling component of the T cell receptor complexes to a level such that T cells have functional HIV-specific cytotoxicity, is provided. The T cells are administered to the mammal in a therapeutically effective amount such that treatment of the HIV infection occurs.

Another aspect of the invention is a pharmaceutical composition for treating HIV infection in a mammal. The composition comprises a therapeutically effective amount of T cells obtained from the mammal, the T cells having been cultured under conditions so as to increase the expression of the CD3$\zeta$ receptor complex component of the T cells to a level such that the T cells have functional HIV-specific cytotoxicity, and a pharmaceutically acceptable carrier.

Yet another aspect of the invention is a test kit suitable for use to determine the immunocompetence of a mammal. The test kit comprises a predetermined amount of a first labeled antibody which binds to CD3$\zeta$, a predetermined amount of a second labeled antibody which binds to CD3$\epsilon$, and directions for use of the kit.

The above and other features, objects and advantages of the present invention will be better understood by a reading of the following specification in conjunction with the drawings.

DETAILED DESCRIPTION

This invention provides a method for determining the immunocompetence of a mammal. Bodily fluid having cells from a mammal, the cells having T cell receptor complexes is provided. The expression of a first component and a second component of the T cell receptor complexes is evaluated. An abnormal ratio of the number of cells expressing the first component as compared to the number of cells expressing the second component indicates altered immunocompetence in the mammal.

By immunocompetence is meant the capacity of the host immune response to control and contain pathogenic infections by viruses, bacteria, fungi and parasites.

By mammal is meant human as well as non-human mammals. Non-human mammals include, e.g., monkeys, chimpanzees, apes, rodents, pigs or rabbits. A mammal is also meant to include transgenic non-human mammals. The term transgenic mammal is meant to include an mammal that has gained new genetic information from the introduction of foreign DNA, i.e., partly or entirely heterologous DNA, into the DNA of its cells; or introduction of a lesion, e.g., an in vitro induced mutation, e.g., a deletion or other chromosomal rearrangement into the DNA of its cells; or introduction of homologous DNA into the DNA of its cells in such a way as to alter the genome of the cell into which the DNA is inserted, e.g., it is inserted at a location which differs from that of the natural gene or its insertion results in a knockout. The mammal may include a transgene in all of its cells including germ line cells, or in only one or some of its cells. Transgenic mammals of the invention can serve as models for studying immunocompetence. A mammal also includes a prenatal mammal.

Bodily fluid is meant to include, e.g., blood, peripheral blood mononuclear cells (PBMCs), T cells, lymph and cells derived from lymphoid organs including lymph nodes, spleen and thymus. Bodily fluid is also meant to include samples or portions of bodily fluid that have been resuspended in other media or pelleted.

T cells are leukocytes. Preferably, the T cells are CD8$^+$. The first step in T cell activation by antigen presenting cells is engagement of the T cell receptor complex. The T cell receptor complex comprises a clonotypic dimeric T cell receptor (TcR), required for antigen recognition, in noncovalent association with CD3, a multicomponent signal transduction complex. CD3 comprises CD3$\delta$, CD3$\epsilon$, CD3$\gamma$ and CD3$\zeta$ chains. CD3$\zeta$ is a chain-containing dimer, which may be a homodimer or heterodimer with CD3$\eta$ or Fc$\epsilon$ receptor $\gamma$ chain. (See Weiss and Littmann, Cell 76:263–274 (1994)).

By signaling component is meant a molecule that transduces the binding of an external molecule to a cell surface receptor and communicates the binding to the interior of the cell. Intracellular receptor signaling components include, e.g., CD3ζ, CD3η and FCε receptor γ chain. Extracellular receptor complex components include, e.g., CD3ε, CD3δ, CD3γ, T cell receptor α and T cell receptor β. Preferably, the first component of the invention is CD3ζ. Preferably, the second component is CD3ε. All known components of the CD3 complex are required for transport of the TcR to the T cell surface. CD3ζ is rapidly cycled from the cell surface, and is important in transmitting the activation signal. CD3ζ is directly associated with Zap70, a protein tyrosine kinase, that is important in transducing the TcR signal.

The invention also includes measuring immunocompetence of a mammal by evaluating expression of a first component and a second component of NK cells. Preferably, the first component is CD3ζ.

By expression of a component is meant expression of the component polypeptide by a cell. In preferred embodiments, evaluation of expression of the first component and the second component of the T cell receptor complexes comprises contacting a first sample of the bodily fluid from the mammal with a first antibody that binds to the first component, and contacting a second sample of the bodily fluid with a second antibody that binds to the second component, under conditions which allow for formation of a first reaction complex comprising the first component and the first antibody, and formation of a second reaction complex comprising the second component and the second antibody. The number of cells expressing the first and second complexes formed is detected. The number of cells expressing the first reaction complex corresponds to the level of the first component in the bodily fluid sample, and the number of cells expressing the second reaction complex corresponds to the level of the second component in the bodily fluid sample. The ratio of the number of cells expressing the first reaction complexes formed to the number of cells expressing the second reaction complexes formed is determined. An abnormal ratio of the number of cells expressing the first component as compared to the number of cells expressing the second component indicates altered immunocompetence in the mammal.

In certain embodiments, CD3ζ and CD3ε are analyzed separately. In certain embodiments, CD3ζ and CD3ε are analyzed together.

Preferably, the antibodies used are monoclonal antibodies. For example, antibodies against CD3ζ, e.g., mAb=6B10.2, can be obtained from Santa Cruz Biotechnology, Inc., Santa Cruz, Calif. (catalog # SC-1239). See also Anderson et al., J. of Immunol. 143:1899–1904 (1989), which describes another mAb, TIA-2. Antibodies against CD3ε, e.g., SK7, can be obtained from Becton Dickinson, San Jose, Calif.

In preferred embodiments, the evaluating step is done in vitro. Preferably, the cells, e.g., the T cells, in the bodily fluid are suspended in a biological inactivating fixing agent prior to contacting the sample with the first and second antibodies. Preferably, only CD3ζ is fixed. The fixing agent can be, e.g., formaldehyde or paraformaldehyde. Preferably, formaldehyde is used. In preferred embodiments, CD3ζ is fixed and CD3ε is not fixed. Preferably, the cells, e.g., the T cells, in the bodily fluid are permeabilized prior to contacting the sample with the first and second antibodies. The cells can be permeabilized, e.g., with absolute methanol, acetone or Caltag a Fix and Perm Kit. Preferably, Caltag Fix and Perm Kit is used.

In preferred embodiments, the antibodies are labeled. The label can be, e.g., radioactive or non-radioactive. Preferably, the label is non-radioactive. Non-radioactive labels include, e.g., fluorescent reagents, e.g., fluorescein isothiocyanate, phycoerythrin or Texas red, or other optically useful non-radioactive reagents. Preferably, fluorescent labels are used. In preferred embodiments, the first antibody is labeled with FITC (fluorescein isothiocyanate) and the second antibody is labeled with PE (phycoerythrin).

Preferably, detection of the amount of first and second reaction complexes formed is by flow cytometry (Weir, D. M., Hergenberg, L. A., Blackwell, C. C. and Hergenberg, L. A. (eds.), The Handbook of Experimental Immunology (4th ed.) Blackwell Scientific, Edinburgh (1986)).

By abnormal ratio of the number of cells expressing the first component as compared to the second component is meant a statistically significant deviation from the ratio obtained from a normal individual. By normal individual is meant an individual with unimpaired immunocompetence. For example, an individual who has deficient immunocompetence as a result of a disease, e.g., HIV infection, exhibits an abnormal ratio of expression of a first component of the T cell receptor complex, e.g., CD3ζ, as compared to a second component of the T cell receptor complex, e.g., CD3ε. In this example, the ratio of CD3ζ to CD3ε is about 1.0 in normal individuals, whereas it is significantly less than 1.0 in HIV-infected individuals at different stages of the disease.

The invention also includes a method for monitoring a therapeutic treatment of a disease in a mammal associated with an abnormal level of a first T cell receptor complex component. The ratio of cells expressing the first T cell receptor complex component and a second T cell receptor complex component in a plurality of bodily fluid samples having cells obtained at different time points from a mammal undergoing a therapeutic treatment for a disease associated with an abnormal level of the first T cell receptor complex component, is determined. A ratio that has become more normal is indicative of an effective therapeutic treatment.

In preferred embodiments, determination of the ratio of expression comprises contacting each of the plurality of bodily fluid samples with a first antibody that binds to a first T cell receptor complex component under conditions which allow for formation of a first reaction complex, and contacting each of the plurality of bodily fluid samples with a second antibody that binds to the second T cell receptor complex component under conditions which allow for formation of a second reaction complex. The number of cells expressing the first and second reaction complexes formed is detected. The number of cells expressing the first reaction complex corresponds to the level of the first component in the bodily fluid sample, and the number of cells expressing the second reaction complex corresponds to the level of the second component in the bodily fluid sample. The ratio of the number of cells expressing the first reaction complexes formed to the number of cells expressing the second reaction complexes formed is determined. A ratio that has become more normal is indicative of an effective therapeutic treatment.

By a more normal ratio is meant a ratio that is closer to the ratio of approximately 1.0 obtained from a normal individual, i.e., an individual that does not have the disease for which the therapeutic treatment is being monitored.

Preferably, the first component is CD3ζ. Preferably, the second component is CD3ε.

The disease can be any disease which is associated with an abnormal level of a T cell receptor complex component.

In preferred embodiments, the disease results from chronic antigen exposure or chronic inflammation. Examples of diseases include HIV infection, Hodgkin's disease and solid tumors. Preferably, the disease is HIV infection. HIV infection is meant to include all stages of infection, including AIDS.

The invention also includes a method for assessing the progression of a disease in a mammal associated with an abnormal level of a first T cell receptor complex component. The ratio of expression of the first T cell receptor complex component and a second T cell receptor complex component in a plurality of bodily fluid samples having cells obtained at different time points from the mammal, is determined. A ratio that becomes more abnormal is indicative of progression of the disease, and a ratio that becomes more normal is indicative of regression of the disease.

Preferably, the first component is CD3ζ. Preferably, the second component is CD3ε. Preferably, the ratio of expression is determined as described above. In preferred embodiments, the disease results from chronic antigen exposure or chronic inflammation. Examples of diseases include HIV infection, Hodgkin's disease and solid tumors. Preferably, the disease is HIV infection.

The invention also includes a method for predicting the prognosis of a mammal having a disease which is associated with an abnormal level of a first T cell receptor complex component. The ratio of cells expressing the first T cell receptor complex component and a second T cell receptor complex component in a plurality of bodily fluid samples having cells obtained at different time points from the mammal is determined. A ratio that becomes more abnormal is indicative of a negative prognosis for the mammal, and a ratio that becomes more normal is indicative of a positive prognosis for the mammal.

The invention also includes a method for determining if a mammal is at risk for AIDS. Bodily fluid having cells from a mammal, the cells having T cell receptor complexes, and the mammal being infected with HIV, is provided. The ratio of cells expressing a first T cell receptor complex component and a second T cell receptor complex component is determined. An abnormal ratio is diagnostic of being at risk for AIDS.

Preferably, the first component is CD3ζ. Preferably, the second component is CD3ε. Preferably, the ratio of expression is determined as described above.

The invention also includes a method for evaluating an agent for use in treating HIV infection. A mammal infected with HIV is provided. The mammal has an abnormal ratio of the number of cells expressing a first T cell receptor complex component as compared to the number of cells expressing a second T cell receptor complex component. An agent is provided. The agent is administered to the mammal in a therapeutically effective amount. The effect of the agent on the ratio of the number of cells expressing the first T cell receptor complex component as compared to the number of cells expressing the second T cell receptor complex component is evaluated. A change in the ratio is indicative of the usefulness of the agent in treating HIV infection.

Preferably, the first component is CD3ζ. Preferably, the second component is CD3ε.

By agent is meant any substance, e.g., an anti-HIV drug. The agent of this invention preferably can change an aspect of the T cell receptor complex metabolism. By T cell receptor complex metabolism is meant any aspect of the production, release, expression, function, action, interaction or regulation of any component of the T cell receptor complex. The metabolism of the T cell receptor complex includes, e.g., modifications, e.g., covalent or non-convalent modifications of a T cell receptor complex component, and covalent or non-covalent modifications that a T cell receptor complex component induces in other substances. The metabolism of the T cell receptor complex also includes changes in the distribution, concentration, activation or phosphorylation of a T cell receptor complex component, and changes that a T cell receptor complex component induces in the distribution, concentration, activation or phosphorylation of other substances.

Examples of agents include polypeptides, e.g., a T cell receptor complex component, or a biologically active fragment or analog thereof; a nucleic acid encoding a polypeptide or a regulatory sequence, or a biologically active fragment thereof; an antisense nucleic acid; a mimetic of a polypeptide; an antibody for a polypeptide; a metabolite; or a carbohydrate or glycoprotein. In certain embodiments, the agent is an antagonist, agonist or super agonist.

The invention also includes the agent so identified as being useful in treating HIV infection.

The invention also includes a method for treating HIV infection in a mammal. A mammal having T cell receptor complexes and in need of treatment for HIV infection is provided. An agent capable of altering the expression of a signaling component of the T cell receptor complex is provided. The agent is administered to the mammal in a therapeutically effective amount such that treatment of the HIV infection occurs.

Preferably, the signaling component is CD3ζ.

Treating is meant to include, e.g., preventing, treating, reducing the symptoms of, or curing the HIV infection. Administration of the agent can be accomplished by any method which allows the agent to reach the target cells. These methods include, e.g., injection, deposition, implantation, suppositories, oral ingestion, inhalation, topical administration, or any other method of administration where access to the target cells by the agent is obtained. Injections can be, e.g., intravenous, intradermal, subcutaneous, intramuscular or intraperitoneal. Implantation includes inserting implantable drug delivery systems, e.g., microspheres, hydrogels, polymeric reservoirs, cholesterol matrices, polymeric systems, e.g., matrix erosion and/or diffusion systems and non-polymeric systems, e.g., compressed, fused or partially fused pellets. Suppositories include glycerin suppositories. Oral ingestion doses can be enterically coated. Inhalation includes administering the agent with an aerosol in an inhalator, either alone or attached to a carrier that can be absorbed.

Administration of the agent can be alone or in combination with other therapeutic agents. In certain embodiments, the agent can be combined with a suitable carrier, incorporated into a liposome, or incorporated into a polymer release system.

In certain embodiments of the invention, the administration can be designed so as to result in sequential exposures to the agent over some time period, e.g., hours, days, weeks, months or years. This can be accomplished by repeated administrations of the agent by one of the methods described above, or alternatively, by a controlled release delivery system in which the agent is delivered to the mammal over a prolonged period without repeated administrations. By a controlled release delivery system is meant that total release of the agent does not occur immediately upon administration, but rather is delayed for some time period. Release can occur in bursts or it can occur gradually and continuously. Administration of such a system can be, e.g., by long acting oral dosage forms, bolus injections, transdermal patches or sub-cutaneous implants.

Examples of systems in which release occurs in bursts include, e.g., systems in which the agent is entrapped in liposomes which are encapsulated in a polymer matrix, the liposomes being sensitive to a specific stimuli, e.g., temperature, pH, light or a degrading enzyme, and systems in which the agent is encapsulated by an ionically-coated microcapsule with a microcapsule core-degrading enzyme. Examples of systems in which release of the agent is gradual and continuous include, e.g., erosional systems in which the agent is contained in a form within a matrix, and diffusional systems in which the agent permeates at a controlled rate, e.g., through a polymer. Such sustained release systems can be, e.g., in the form of pellets or capsules.

The agent can be suspended in a liquid, e.g., in dissolved form or colloidal form. The liquid can be a solvent, partial solvent or non-solvent. In many cases water or an organic liquid can be used.

The agent can be administered prior to or subsequent to the appearance of symptoms associated with HIV infection.

The agent is administered to the mammal in a therapeutically effective amount. By therapeutically effective amount is meant that amount which is capable of at least partially preventing or reversing HIV infection. A therapeutically effective amount can be determined on an individual basis and will be based, at least in part, on consideration of the species of mammal, the mammal's size, the mammal's age, the agent used, the type of delivery system used, the time of administration relative to the onset of HIV symptoms, and whether a single, multiple, or controlled release dose regimen is employed. A therapeutically effective amount can be determined by one of ordinary skill in the art employing such factors and using no more than routine experimentation.

Preferably, the concentration of the agent is at a dose of about 0.1 to about 1000 mg/kg body weight, more preferably at about 0.1 to about 500 mg/kg, more preferably yet at about 0.1 to about 100 mg/kg, and most preferably at about 0.1 to about 5 mg/kg. The specific concentration partially depends upon the particular agent used, as some are more effective than others. The dosage concentration of the agent that is actually administered is dependent at least in part upon the final concentration that is desired at the site of action, the method of administration, the efficacy of the particular agent, the longevity of the particular agent, and the timing of administration relative to the onset of the HIV symptoms. Preferably, the dosage form is such that it does not substantially deleteriously affect the mammal. The dosage can be determined by one of ordinary skill in the art employing such factors and using no more than routine experimentation.

In certain embodiments, various gene constructs can be used as part of a gene therapy protocol to deliver nucleic acids encoding, e.g., either an agonistic or antagonistic form of a T cell receptor complex component. Expression vectors can be used for in vivo transfection and expression of a component polypeptide in particular cell types so as to reconstitute the function of, or alternatively, abrogate the function of the component in a cell in which non-wild type component is expressed. Expression constructs of the component polypeptide, and mutants thereof, may be administered in any biologically effective carrier, e.g. any formulation or composition capable of effectively delivering the nucleic acid to cells in vivo. Approaches include, e.g., insertion of the subject nucleic acid in viral vectors including, e.g., recombinant retroviruses, adenovirus, adeno-associated virus, and herpes simplex virus-1, or recombinant bacterial or eukaryotic plasmids. Viral vectors transfect cells directly; plasmid DNA can be delivered with the help of, for example, cationic liposomes (lipofectin) or derivatized (e.g. antibody conjugated), polylysine conjugates, gramacidin S, artificial viral envelopes or other such intracellular carriers, as well as direct injection of the nucleic acid construct or $CaPO_4$ precipitation carried out in vivo. The above-described methods are known to those skilled in the art and can be performed without undue experimentation. Since transduction of appropriate target cells represents the critical first step in gene therapy, choice of the particular gene delivery system will depend on such factors as the phenotype of the intended target and the route of administration, e.g., locally or systemically. Administration can be directed to one or more cell types, and to one or more cells within a cell type, so as to be therapeutically effective, by methods that are known to those skilled in the art.

The invention also includes a method for treating HIV infection in a mammal. A mammal having T cell receptor complexes and in need of treatment for HIV infection is provided. T cells which have been cultured under conditions so as to increase the expression of a signaling component of the T cell receptor complexes to a level such that T cells have functional HIV-specific cytotoxicity, are provided. The T cells are administered to the mammal in a therapeutically effective amount such that treatment of the HIV infection occurs.

Preferably, the T cells are obtained from the same mammal that is to be treated, by standard methods known to those skilled in the art. The conditions under which the T cells are cultured can be any conditions which result in the T cells having functional HIV-specific cytotoxicity. Preferably, the T cells are cultured for a period of 14 hours to 72 hours, more preferably 14 hours to 24 hours, and most preferably 15 hours to 18 hours. In preferred embodiments, cells are cultured at 37° C. over 4–7% $CO_2$ at a density of about 5–20×10$^6$ cells/ml in RPMI 1640 media containing a source of serum or in serum-free media designed to support T cell culture. Cells may be grown in flasks, gas-permeable bags or hollow fiber cartridges. For example, normalization of the CD3ζ/CD3ε ratio occurs after overnight culture (about 16 hours) and coincides with restoration of HIV-specific cytotoxicity. See Examples 3 and 4.

The T cells are administered in a therapeutically effective amount, as can be determined by one of ordinary skill in the art. Preferably, the concentration of T cells is about 1 billion to about 100 billion, more preferably about 1 billion to about 10 billion, and most preferably about 1 billion to about 5 billion.

The invention also includes a pharmaceutical composition for treating HIV infection in a mammal. The composition comprises a therapeutically effective amount of T cells obtained from the mammal, the T cells having been cultured under conditions so as to increase the expression of the CD3ζ receptor complex component of the T cells to a level such that the T cells have functional HIV-specific cytotoxicity, and a pharmaceutically acceptable carrier.

The invention also includes a test kit suitable for use to determine the immunocompetence of a mammal. The test kit comprises a predetermined amount of a first labeled antibody which binds to CD3ζ, a predetermined amount of a second labeled antibody which binds to CD3ε, and directions for use of the kit. Preferably, the first and second labeled antibodies are labeled with a fluorescent reagent. In certain embodiments, the test kit also comprises a cell fixing reagent. In certain embodiments, the test kit also comprises a cell permeabilization reagent. In certain embodiments, the kit also comprises media for contacting the first and second antibodies with test cells so as to permit formation of reaction complexes between the first antibody and the test cells, and the second antibody and the test cells. In certain embodiments, the kit also comprises a first isotype antibody of the first labeled antibody and a second isotype antibody of the second labeled antibody. In certain embodiments, the kit also comprises a reagent to lyse red blood cells so that isolation of PBMCs is not necessary. The kit also can have wash media and/or tubes.

The following non-limiting examples further illustrate the present invention.

EXAMPLES

Example 1
A large fraction of circulating T cells from symptomatic HIV-infected individuals have deficient CD3ζ expression This examples illustrates that the ratio of CD3ζ expression compared to CD3ε expression is significantly lower in T cells from symptomatic HIV-infected individuals as compared to normal individuals. Subjects were normal volunteers or HIV-1 seropositive patients of varied disease stage, as shown in Table 1.

TABLE 1

Clinical Characteristics of Subjects

| Subject | CDC Disease Stage | CD4 Count (cells/mm$^3$) | Clinical symptoms |
|---|---|---|---|
| 203 | B2 | 490 | hx thrush |
| 214 | B2 | 220 | OHL, hx thrush |
| 216 | C3 | 50 | hx PCP pneumonia, KS |
| 219 | A2 | 370 | generalized lymphadenopathy |
| 228 | B3 | 194 | hx thrush |
| 234 | A2 | 230 | none |
| 235 | C3 | 7 | hx PCP pneumonia, esophageal candidiasis |
| 237 | B2 | 260 | hx atypical mycobacterial bursitis |
| 307 | B2 | 283 | hx thrush |
| 346 | A1 | normal | none |
| 348 | A1 | normal | none |
| 350 | A1 | normal | none |
| 351 | A1 | normal | none |

HIV-infected donors were either treated by a private practitioner with combination antiretroviral drugs and IFNα shortly after seroconversion, or were subjects enrolled in the NIH Division of AIDS Treatment Research Initiative (DATRI) protocol 006. For the latter, samples were mostly obtained prior to treatment with autologous T cell infusion. A few samples were obtained for at least 3–12 months after an infusion. Samples were either freshly obtained or cryopreserved using a programmed cell freezer (Cordinier Model 9000, Roseville, Mich.). Flow cytometry results obtained from thawed cells were comparable to those from freshly isolated cells in two samples studied.

PBMC samples were obtained from the HIV-infected donors by Ficoll-Hypaque density centrifugation. The PBMC samples were directly stained with immunofluorescent antibody to cell surface CD3ε or isotype matched control antibody and were permeabilized and indirectly stained with antibody to CD3ζ or control, and flow cytometry was performed.

For CD3ε staining, PBMC (approximately 2–10×10$^5$/tube), isolated by Ficoll-Hypaque density centrifugation from heparinized blood, were suspended in 50 μl FACS (fluorescence-activated cell sorting) buffer (2% fetal calf serum, 0.2 mg/ml NaN$_3$ in PBS) in a 1.2 ml Eppendorf tube to which 4 μl PE-conjugated CD3ε SK7 mAb (Becton Dickinson, Mountain View, Calif.) or isotype matched control was added. After incubation for 20 minutes at 4° C. in the dark, cells were washed with 1 ml FACS buffer and resuspended in FACS buffer with 1% formaldehyde to fix, for about 1 hour, prior to analysis.

For CD3ζ staining, cells were resuspended in 50 μl PBS at a concentration of about 2–10×10$^5$/50 μl in a 15 ml conical tube. 100 μl of Reagent A (Fixation Medium) from Caltag Laboratories, Fix and Perm Cell Permeabilization Kit (catalog # GAS-004) (Caltag Laboratories, Burlingame, Calif.) was added according to the manufacturer's protocol, and incubated for 15' at room temperature. 5 ml PBS was added to each tube and centrifuged at 300 g for 5 min. The pellet was resuspended in 100 μl Reagent B (Permeabilization Medium) and 50 μl was transferred to a second 15 ml conical tube. 2 μl CD3ζ mAb 6B10.2 (Santa Cruz, Santa Cruz, Calif.) was added to one tube and 2.5 μl MsIgG1 isotype-matched control antibody (Coulter, Hialeah, Fla., catalog # SC-21239) was added to the other tube. After three washes of 5 ml PBS, the cells were resuspended in 50 μl Reagent B. The cells were stained with 2 μl RPE-conjugated F(ab')$_2$ goat anti-mouse Ig (DAKO Corporation, Carpinteria, Calif., catalog #R 0480). After two further washes, cells were resuspended in PBS with 1% formaldehyde for analysis.

Figure 1:
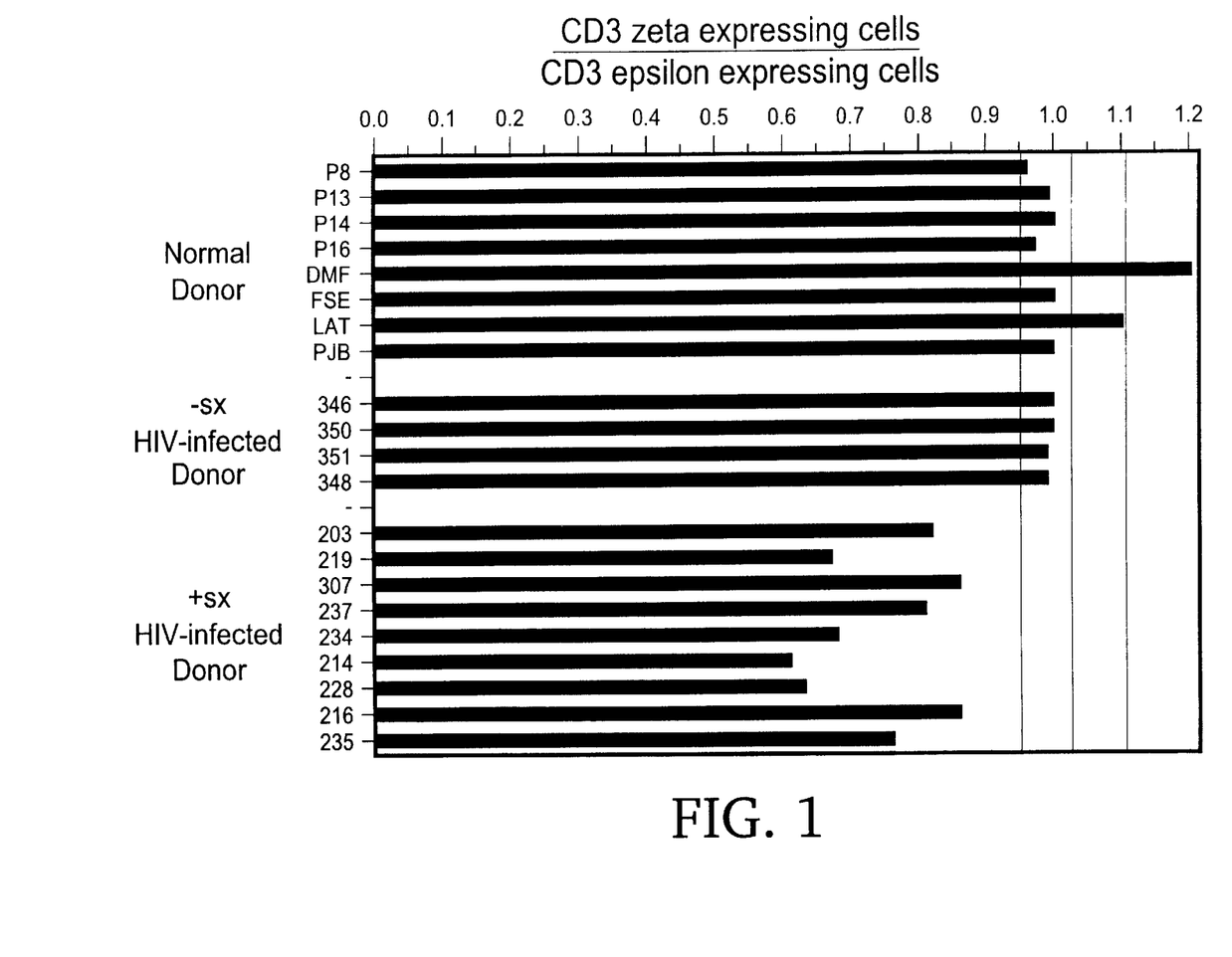
FIG. 1 depicts the ratio of the number of CD3$\zeta$ expressing T cells to the number of CD3$\epsilon$ expressing T cells in normal and HIV-infected individuals.

Flow cytometry analysis was performed on a tightly gated lymphocyte population using FACscalibur (Becton Dickinson). Cellquest (Becton Dickinson) software was used to overlay and subtract the histograms of the negative isotype control antibody-stained cells from the CD3ζ stained cells. For each sample the ratio of the number of cells staining for CD3ζ to those staining for CD3ε was calculated. See FIG. 1.

In PBMC from normal donors, the number of cells expressing CD3ζ corresponded to the number of CD3ε expressing cells. The ratio of CD3ζ expressing cells to CD3ε expressing cells in eight normal donor samples was 1.03±0.08, not significantly different from the expected value of 1. See FIG. 1.

PBMC from nine HIV-infected donors of varying disease stage (see Table 1) were analyzed. All of these subjects had evidence of disease by reduced CD4 counts (range 7–490 cells/mm$^3$), one had no clinical symptoms, one had generalized lymphadenopathy, six had minor infections characteristic of HIV infection and three met the CDC criteria for AIDS. The ratio of CD3ζ expressing cells to CD3ε expressing cells in these subjects was significantly reduced with a range from 0.61–0.82 and a mean value of 0.73±0.08. This was statistically different from the value for normal volunteers by 2-sided t-test (p<0.001).

PBMC from four recent seroconvertors who had been aggressively treated with combination antiretroviral drugs and IFN α and who had undetectable plasma viral RNA (<500 copies/ml) and well maintained CD4 counts, were also analyzed. T cells from these four subjects had normal ratios (1.00±0.01). Therefore, an abnormal ratio does not develop after the primary infection, but coincides with early changes in immunocompetence.

Additional experiments indicate that similar results are obtained with isolated CD8$^+$ T cells.

Example 2
A large fraction of circulating T cells from symptomatic HIV-infected individuals lack HIV-specific cytotoxicity This example illustrates that a large fraction of the T cells from symptomatic HIV-infected individuals lack HIV-specific cytotoxicity.

T cell lines were generated by overnight culture of PBMC at 5×10$^5$/ml in T cell medium (RPMI 1640 supplemented with 2 mM glutamine, 2 mM HEPES, 100 U/ml penicillin, 100 ug/ml streptomycin and 50 uM β-mercaptoethanol) to which was added either 10% fetal calf serum or autologous patient plasma. In some cases recombinant human interleukin-2 (rhuIL-2, Cetus, Emeryville, Calif.) was added to the medium at varying concentrations. In some cases HIV-1$_{LAI}$ was added at a multiplicity of infection of 0.05 at the initiation of culture. Autologous B lymphoblastoid cell lines (B-LCL) were generated for each subject using standard methods.

HIV-specific cytotoxicity of PBMC, freshly isolated or after overnight culture, was analyzed by 4 hr $^{51}$Cr release assay against autologous B-LCL targets infected with vaccinia recombinant vectors encoding HIV genes as previously described. Target cells were infected with vaccinia vectors encoding lacZ (vSC8), env of the BH8 isolate of HIV-1$_{IIIB}$ (vPE16), gag of the HXB.2 subclone (vDK1), and all but the last 22 residues of HXB.2 RT (vCF21).

In most symptomatic HIV-infected individuals there was no detectable HIV-specific cytotoxicity as measured by chromium release assay, above background.

Example 3
HIV-specific cytotoxicity in symptomatic HIV-infected individuals is greatly enhanced by overnight in vitro culture This example illustrates that culturing T cells obtained from symptomatic HIV-infected individuals overnight in vitro greatly enhances the HIV-specific cytotoxicity of the T cells.

The kinetics and IL-2 dependence of emergence of viral specific cytotoxic activity in vitro was determined by measuring specific cytotoxicity against HIV-expressing autologous targets, HIV-1 env, HIV-1 pol and HIV-1 gag, after overnight and three day culture in IL-2 containing media by PBMC from two subjects whose freshly isolated PBMC lacked significant activity. The protocol used for measuring cytotoxicity against the targets was as described in Lieberman et al., J. Immunol. 148:2738–2747 (1992).

Figure 2:
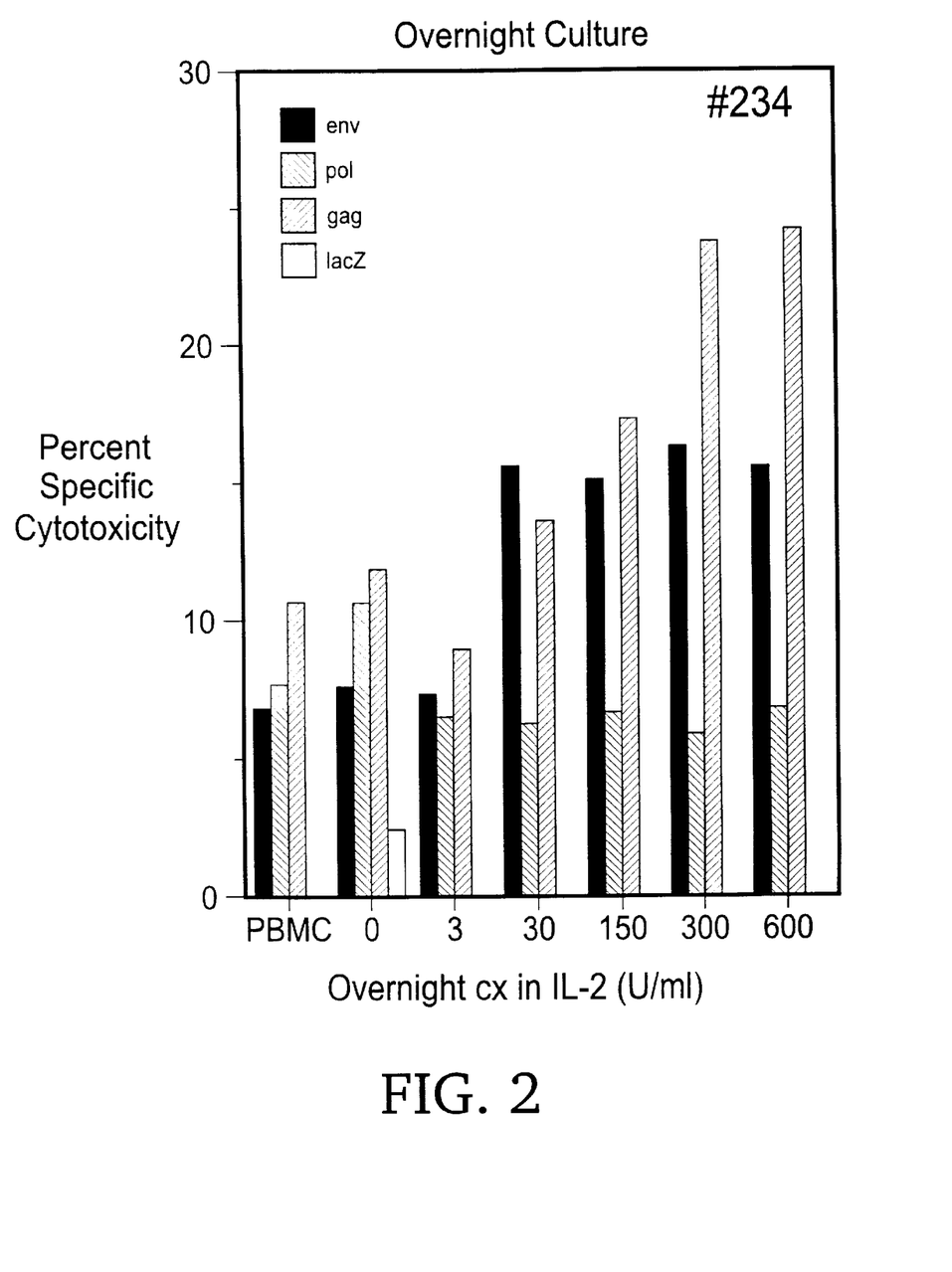
FIG. 2 depicts the kinetics of recovery and IL2 dependence of HIV-specific cytotoxicity resulting from in vitro overnight culturing of T cells by measuring specific cytotoxicity against HIV-expressing autologous targets, env, pol and gag.
Figure 3:
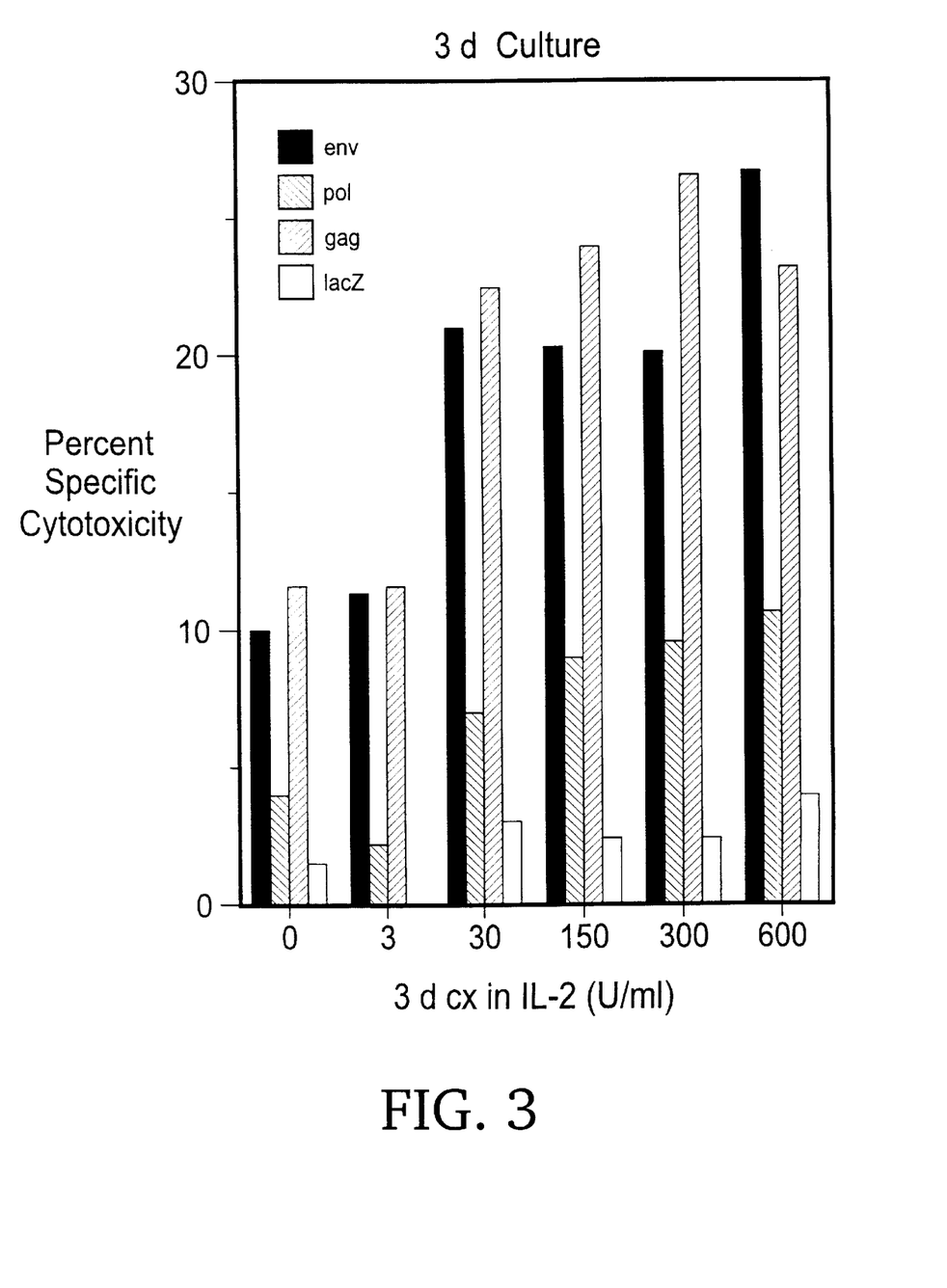
FIG. 3 depicts the kinetics of recovery and IL2 dependence of HIV-specific cytotoxicity resulting from in vitro three day culturing of T cells by measuring specific cytotoxicity against HIV-expressing autologous targets, env, pol and gag.

The results are shown in FIG. 2 and FIG. 3. Antiviral cytotoxic activity emerged after overnight culture to levels comparable to those detected after 2–3 weeks of culture. Since one could expect at most one cell division in this short time, this finding indicates that the development of antiviral cytotoxicity is not dependent on the selective proliferation of HIV-specific precursor CTL in these cultures. The development of viral-specific cytotoxicity occurred in both subjects in an IL-2 dependent manner, reaching a plateau at approximately 300 U/ml IL-2.

Example 4
CD3ζ expression from symptomatic HIV-infected individuals is normalized by overnight in vitro culture This example illustrates that culturing T cells obtained from symptomatic HIV-infected individuals overnight in vitro normalizes CD3ζ expression as measured by comparing the ratio of CD3ζ expression to CD3ε expression.

T cell lines were generated by overnight culture of PBMC at 5×10$^5$/ml in T cell medium (RPMI 1640 supplemented with 2 mM glutamine, 2 mM HEPES, 100 U/ml penicillin, 100 ug/ml streptomycin and 50 uM β-mercaptoethanol) to which was added either 10% fetal calf serum or autologous patient plasma. In some cases recombinant human interleukin-2 (rhuIL-2, Cetus, Emeryville, Calif.) was added to the medium at varying concentrations. In some cases HIV-1$_{LAI}$ was added at a multiplicity of infection of 0.05 at the initiation of culture. Autologous B lymphoblastoid cell lines (B-LCL) were generated for each subject using standard methods.

Figure 4:
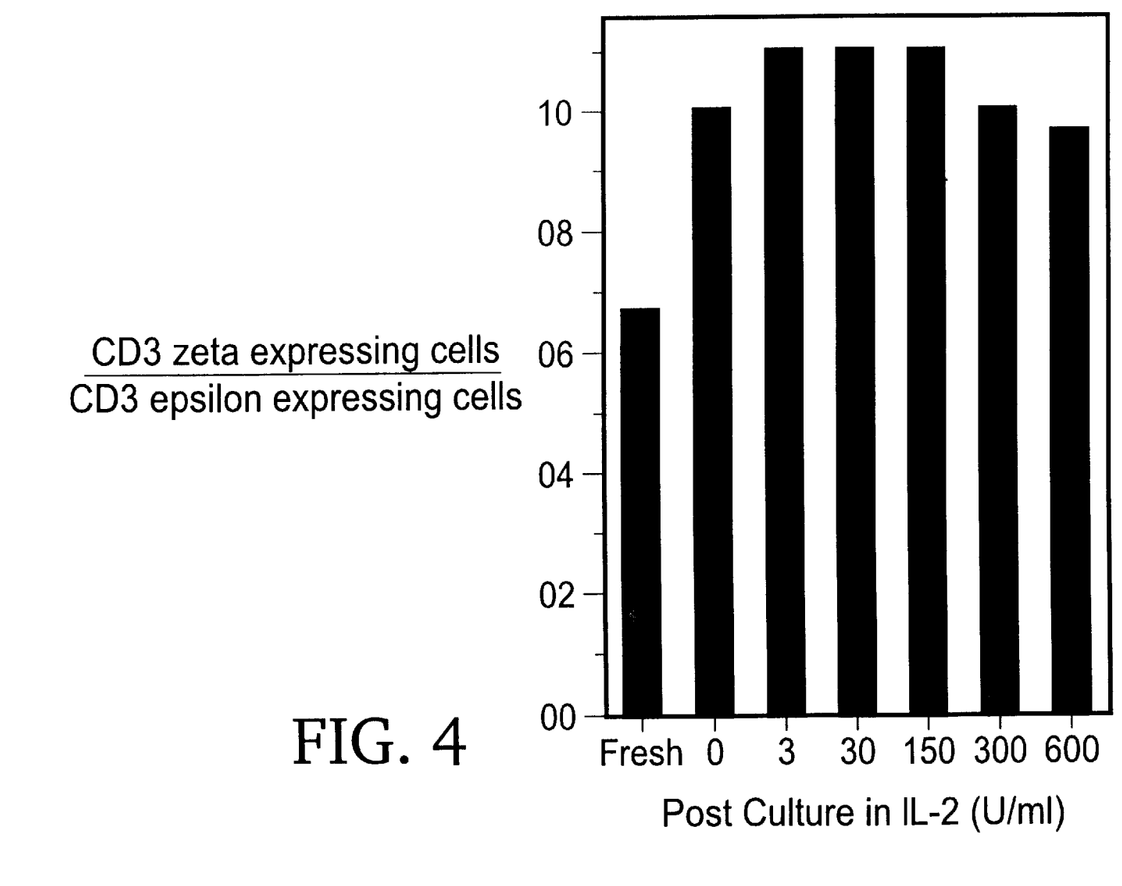
FIG. 4 depicts the ratio of the number of CD3$\zeta$ expressing T cells to the number of CD3$\epsilon$ expressing T cells from HIV-infected individuals in varying disease stages after overnight culture in media with various additions.
Figure 5:
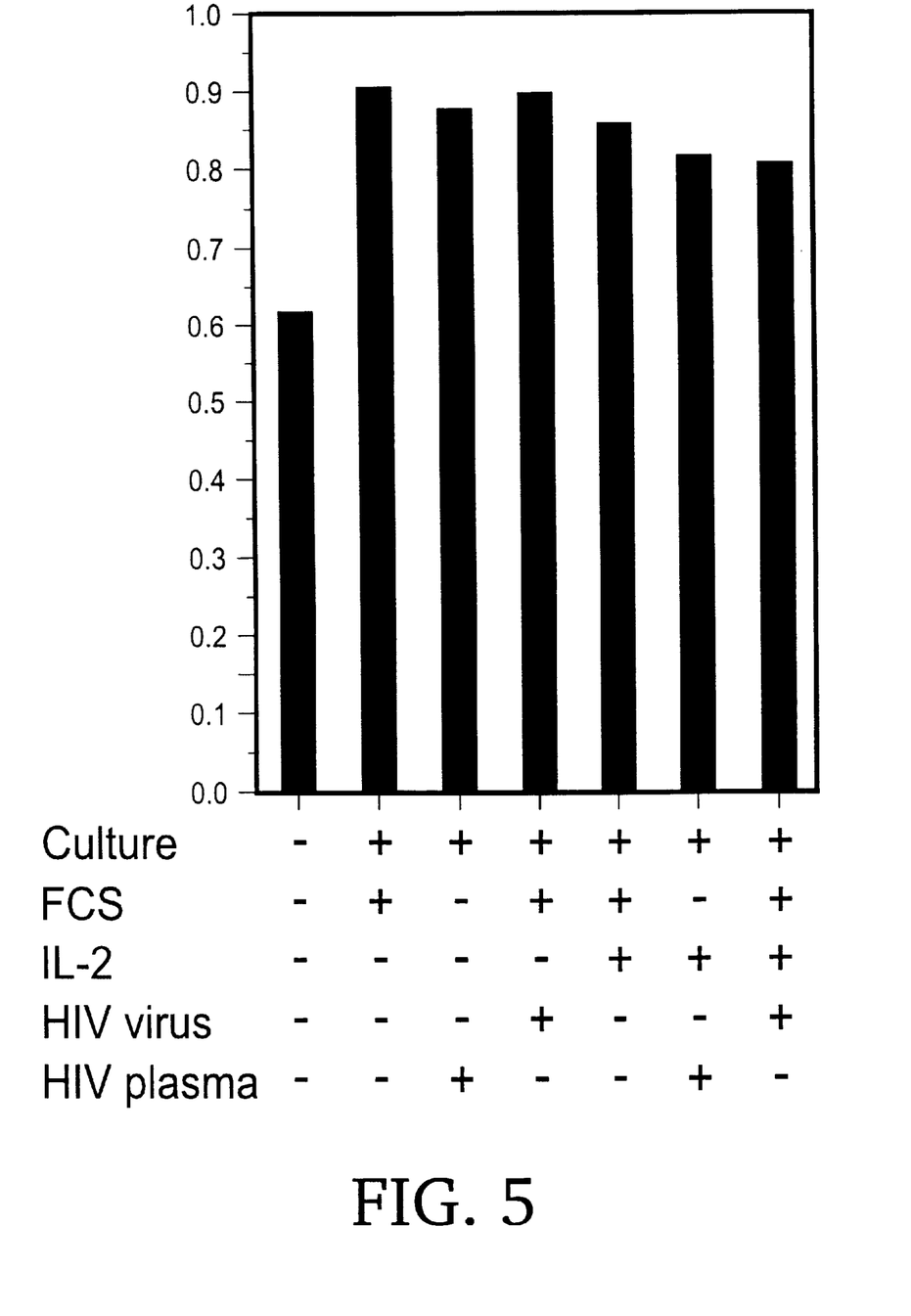
FIG. 5 depicts the ratio of the number of CD3$\zeta$ expressing T cells to the number of CD3$\epsilon$ expressing T cells from HIV-infected individuals in varying disease stages after overnight culture in media with various additions.
Figure 6:
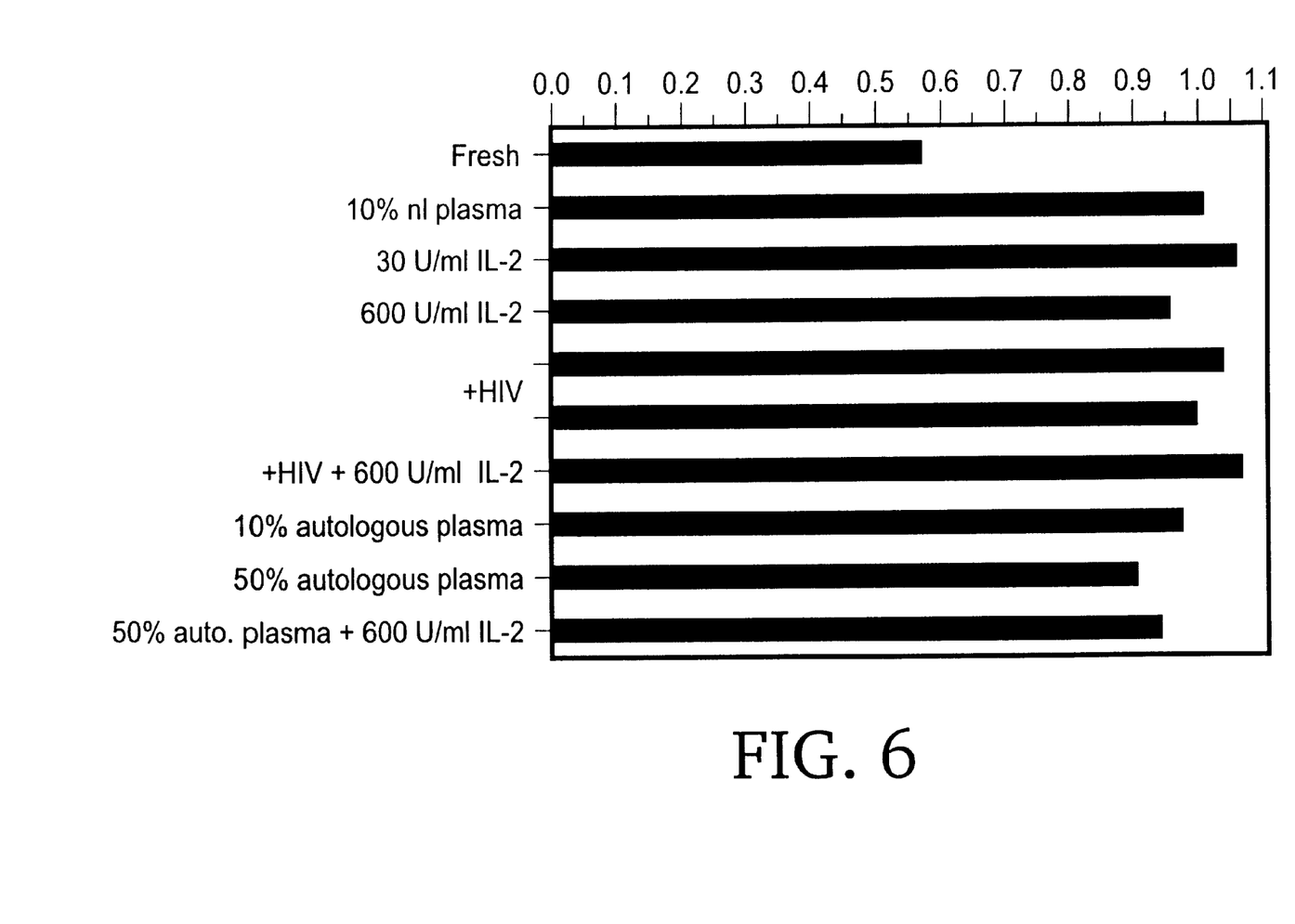
FIG. 6 depicts the ratio of the number of CD3$\zeta$ expressing T cells to the number of CD3$\epsilon$ expressing T cells from HIV-infected individuals in varying disease stages after overnight culture in media with various additions.

Overnight culture in media normalized the CD3ζ expression in PBMC from HIV-infected individuals in varying disease stages. See FIGS. 4, 5 and 6.

Example 5
Deficient CD3ζ expression becomes evident at a very early stage of immunodeficiency This example illustrates that the ratio of CD3ζ expression compared to CD3ε expression becomes abnormal in patients with reduced CD4 counts and early symptoms of AIDS related immunodeficiency, e.g., thrush or oral hairy leukoplakia. See Table 1. Experiments were performed as described in Example 1.

Example 6
Treating an HIV-infected individual with cultured T cells

This example illustrates a method for treating an HIV-infected individual with T cells obtained from that individual that have been cultured in vitro for 16 hours. T cells are obtained from the individual by leukopheresis. The T cells are cultured in RPMI 1640 media at 37° C. over 5% $CO_2$ for 16 hours. The washed T cells (1 billion cells resuspended in 150 mls Plasma Lyte (Baxter)) are administered to the individual intravenously over one hour. This treatment results in alleviation of the HIV infection.

Those skilled in the art will be able to ascertain using no more than routine experimentation, many equivalents of the specific embodiments of the invention described herein. These and all other equivalents are intended to be encompassed by the following claims.

What is claimed is:

1. A method for determining or monitoring HIV infection in a mammal, comprising:

providing cells from a mammal, said cells having T cell receptor complexes, and measuring the expression of a CD3ζ and a CD3ε component of said T cell receptor complexes, wherein the ratio of the number of said cells expressing said CD3ζ as compared to the number of said cells expressing said CD3ε is inversely correlated with HIV infection in said mammal.

2. The method of claim 1 wherein said cells are peripheral blood mononuclear cells.

3. The method of claim 1 wherein said cells having T cell receptor complexes are CD8 positive T cells.

4. The method of claim 1 wherein said measuring step comprises:

contacting a sample comprising said cells with a first antibody that binds to said CD3ζ under conditions which allow for formation of a first reaction complex comprising said CD3ζ and said first antibody; contacting a second sample comprising said cells with a second antibody that binds to said CD3ε under conditions which allow for formation of a second reaction complex comprising said CD3ε and said second antibody;

detecting the number of said cells expressing said first and second reaction complexes formed, wherein said number of cells express said first reaction complex indicates the level of said CD3ζ in said sample and said number of cells expressing said second reaction complex indicates the level of said CD3ε in said sample; and determining the ratio of said number of cells expression said first reaction complexes formed to said number of cells expressing said second reaction complexes formed.

5. The method of claim 4, wherein said measuring step is done in vitro.

6. The method of claim 4 wherein said cells are suspended in a biological inactivating fixing agent prior to contacting said sample with said first and second antibodies.

7. The method of claim 4 wherein said cells are permeabilized prior to contacting said sample with said first and second antibodies.

8. The method of claim 4 wherein said detecting step is by flow cytometry.

9. The method of claim 4 wherein said first antibody is labeled with a fluorescent reagent.

10. The method of claim 4 wherein said second antibody is labeled with a fluorescent reagent.

11. The method of claim 4, wherein a reduction in the ratio of the number of cells expressing the first reaction complexes to the number of cells expressing the second reaction complexes indicates the presence of HIV infection.

12. A method for determining or monitoring an infection selected from the group consisting of a viral, a bacterial, a fungal and a parasitic infection, in a mammal, comprising:

providing cells from a mammal, said cells having T cell receptor complexes, and measuring the expression a first component and a second component of said T cell rector complexes, said first component being CD3ζ, and said second component being selected from the group consisting of CD3ε, CD3δ, CD3γ, T cell receptor α and T cell receptor β, wherein the ratio of the number of said cells expressing said first component as compared to the number of said cells expressing said second component is inversely correlated with said infection in said mammal.

13. The method of claim 12, wherein said second component is CD3δ.

14. The method of claim 12, wherein said second component is CD3γ.

15. The method of claim 12, wherein said second component is T cell receptor α.

16. The method of claim 12, wherein said second component is T cell receptor β.

17. The method of claim 12, wherein said infection is a viral infection.

18. A method for determining or monitoring a disease resulting from chronic antigen exposure in a mammal, comprising:

providing cells from a mammal, said cells having T cell receptor complexes, and measuring the expression a first component and a second component of said T cell receptor complexes, said first component being CD3ζ, and said second component being selected from the group consisting of CD3ε, CD3δ, CD3γ, T cell receptor α and T cell receptor β, wherein the ratio of the number of said cells expressing said first component as compared to the number of said cells expressing said second component is inversely correlated with the disease in said mammal.

19. A method for determining or monitoring a viral infection in a mammal, comprising:

providing cells from a mammal, said cells having T cell receptor complexes, and measuring the expression of a first component and a second component of said T cell receptor complexes, said first component being CD3ζ, and said second component being selected from the group consisting of CD3ε, CD3δ, CD3γ, T cell receptor α and t cell receptor β, wherein the ratio of the number of said cells expressing said first component as compared to the number of said cells expressing said second component is inversely correlated with the viral infection in said mammal.

* * * * *

UNITED STATES PATENT AND TRADEMARK OFFICE
CERTIFICATE OF CORRECTION

PATENT NO.    : 6,197,531 B1                                      Page 1 of 1
DATED         : March 6, 2001
INVENTOR(S)   : Dr. Judy Lieberman It is certified that error appears in the above-identified patent and that said Letters Patent is hereby corrected as shown below:

Title page,
In the title, the word "METHOD" should be -- METHODS -- as follows:
-- [54] METHODS FOR DETERMINING THE IMMUNOCOMPETENCE OF A MAMMAL AND THERAPIES RELATED THERETO --

OTHER PUBLICATIONS, the "Weiss and Littmann, ..." the publication reference "Cell 76-263-274" should read -- Cell 76:263-274 --

Column 4,
Line 37, change "an" to -- any --

Column 12,
Line 25, change "SC-21239" to -- SC-1239 --

Column 14,
Line 67, change "express" to -- expressing --

Column 15,
Line 14, change "expression" to -- expressing --

Column 16,
Line 33, change "t" to -- T --

Signed and Sealed this

Twenty-third Day of April, 2002

*Attest:*

JAMES E. ROGAN
*Attesting Officer*      *Director of the United States Patent and Trademark Office*